United States Patent [19]

Oka et al.

[11] Patent Number: 4,800,165
[45] Date of Patent: Jan. 24, 1989

[54] METHOD OF DETECTING CORROSION RATE OF MEMBER OF STEEL MATERIAL

[75] Inventors: Tomoki Oka; Hiroshi Kihira; Kazumi Matsuoka; Satoshi Ito, all of Kawasaki, Japan

[73] Assignee: Nippon Steel Corporation, Tokyo, Japan

[21] Appl. No.: 1,734

[22] Filed: Jan. 9, 1987

[30] Foreign Application Priority Data

Jan. 11, 1986 [JP] Japan .................................. 61-3905

[51] Int. Cl.[4] ..................... G01N 17/00; G01N 31/00; G01R 27/02
[52] U.S. Cl. .......................................... 436/6; 422/53; 201/1; 324/65 CR
[58] Field of Search ............. 436/6; 324/65 CR, 65 P, 324/444, 445, 446; 204/1 C; 422/53

[56] References Cited

U.S. PATENT DOCUMENTS 4,238,298 12/1980 Tsuru et al. ............................. 204/1
4,667,150 5/1987 Hausler et al. .................. 324/65 CR

FOREIGN PATENT DOCUMENTS 2527772 2/1983 France ................................... 324/65
55-47433 4/1980 Japan .

OTHER PUBLICATIONS

Zen et al., Technical Note of The Port and Harbor Research Institute Ministry of Transportation, Japan, Mar. 1982, p. 5.

Primary Examiner—Barry S. Richman
Assistant Examiner—Lyle Alfandary-Alexander
Attorney, Agent, or Firm—Pollock, Vande Sande & Priddy

[57] ABSTRACT

A method of detecting the rate of corrosion of an existing steel structure installed in a corrosive environment is disclosed. The method includes treating a measurement surface of the member so that an AC impedance of the measurement surface, when electrochemically measured at a predetermined high frequency range of potential variation applied to the measured surface, takes a first valve within a predetermined range; and second value of the impedance is then electrochemically measured at a low frequency range of potential variation applied thereto. The difference between the first and second values is calculated to detect the corrosion-reaction resistance of the surface and the rate of corrosion is determined on the basis of the detected corrosion-reaction resistance and according to a pre-calculated relation between the rate of corrosion and the corrosion-reaction resistance.

3 Claims, 3 Drawing Sheets

METHOD OF DETECTING CORROSION RATE OF MEMBER OF STEEL MATERIAL

BACKGROUND OF THE INVENTION

This invention relates to a method of corrosion rate detection used for diagnosing deterioration, attributable to corrosion, of civil engineering structural members of steel material, especially, those installed in a corrosive environment such as seawater or river water.

The useful service life of a structural member of steel material used in a corrosive environment, such as, that partly submerged in seawater or river water is necessarily limited due to formation of pits or reduction of its thickness by corrosion. On the other hand, it is desirable that such a structural member can be used for a longest possible period of time from the economical aspect, as long as it is not rendered dangerous as part of structure. Therefore, there is a growing demand for detecting the present status of corrosion of the structural member and diagnosing the degree of corrosion for the purpose of estimating its residual service life. It is indispensable for the diagnosis of the status of corrosion to accurately detect the rate of corrosion.

Various methods are now employed for the detection of the rate of corrosion of such a structural member. According to a first method, a small test piece for corrosion monitoring purpose is previously attached to an equipment or a structural member of steel material, and is periodically checked to find a decrease in the weight due to corrosion, and the value of the decreased weight is divided by the period of the test to detect the rate of corrosion of the equipment or structural member. According to a second method, for example, a method described in a paper entitled "Technical Note of the Port and Harbour Research Institute" No. 413, page 5 (1982), the plate thickness of a structural member of steel material is measured by an ultrasonic thickness gauge, and the difference between the remaining plate thickness and the initial plate thickness of the structural member is divided by the period of use to detect the rate of corrosion of the structural member. According to a third method, for example, a method described in JP-A-55-47433, published on Apr. 3, 1980 a pair of test pieces made of the same material as that of an object whose corrosion rate is to be measured are placed in an environment in which the object is installed, and the rate of corrosion of the object is detected on the basis of an electrochemically measured impedance between the test pieces.

However, data obtained by the first and third methods provide merely information of the rate of corrosion of small test pieces and do not reflect the actual rate of corrosion of an equipment or a structural member itself. Thus, such information is not indicative of the true rate of corrosion of the equipment or structural member itself. Although the second method is more practical than the first and third methods, the initial plate thickness of a structural member is not usually previously measured in most cases, and reference to the plate thickness is usually obtained from known data printed in a catalog. However, tolerance of the plate thickness is allowed in JIS A5525 (Japanese Industrial Standards), and the reference to the catalog data including the tolerance may lead to the cause of an error.

Further, when a paint or like layer is previously coated on the surface of a structural member of steel material for the purpose of temporarily preventing corrosion or when a structural member of steel material is considerably corroded, measurement of the plate thickness by an ultrasonic thickness gauge leads to an error which adversely affects the calculation of the rate of corrosion. Further, the third method is not necessarily efficient in that measurement over an entire available frequency range is required because the frequency response characteristic of the phenomenon of corrosion has not yet been clarified.

SUMMARY OF THE INVENTION

The present invention contemplates a method of corrosion rate detection which detects directly, on the site and at any moment, the rate of corrosion of a structural member of steel material placed in a corrosive environment instead of detecting an average rate of corrosion, which shortens the period of time required for electrochemical measurement thereby enhancing the efficiency of detection of the rate of corrosion, and in which the same conditions are maintained throughout the process of measurement so as to improve the accuracy of the measurement.

The results of researches and studies made by the inventors have clarified the fact that the following conditions are required for detecting the rate of corrosion useful for the diagnosis of corrosion of a structural member of steel material:

(1) In order to avoid any error attributable to the tolerance of the initial plate thickness of the structural member or a paint or like layer coated for the purpose of temporarily preventing corrosion, data of the present rate of corrosion of the structural member, instead of the average of data measured in the past, should be employed.

(2) In order to improve the efficiency of the electrochemical measurement when the electrochemical measurement is carried out to detect an AC impedance of a corroded surface of the structural member, the impedance-frequency characteristic should be investigated to determine the optimum frequency range used for the measurement, thereby avoiding any wasteful measurement in an unnecessary frequency range and shortening the period of time required for the measurement.

(3) How the electrochemical measurement is affected by an oxidation-reduction reaction occurring in a rust layer formed on the surface of the structural member should be evaluated so that the same conditions can be maintained throughout the process of measurement.

It is a primary object of the present invention to provide a method of detecting the rate of corrosion of a structural member of steel material, which satisfies all of the conditions described above.

In the method of corrosion rate detection according to the present invention, a known corrosion rate detector commonly used for on-site measurement of the present rate of corrosion of metal materials is utilized for detecting the rate of corrosion of a civil-engineering structural member of steel material installed in a corrosive environment such as seawater or river water. First, a corroded surface to be subjected to corrosion rate measurement is previously adjusted or treated so that it shows an AC impedance of 5 $\Omega cm^2$ to 50 $\Omega cm^2$ per unit area of the corroded surface when measured electrochemically at a frequency range of 100 Hz to 1,000 Hz by using the above-mentioned detector. Then, while changing the frequency in a specific high frequency range and in a specific low frequency range according to an electrochemical method of measurement such as an AC impedance method or a pulse method, the impedance of the corroded surface is measured to determine the rate of corrosion of the corroded surface on the basis of the measured impedance value.

DESCRIPTION OF THE PREFERRED EMBODIMENTS

Figure 1:
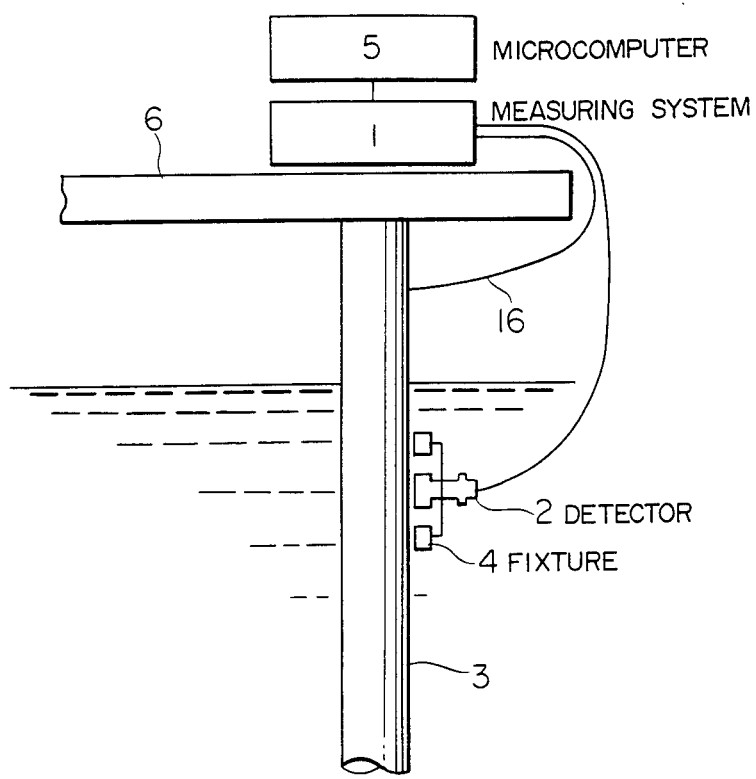
FIG. 1 shows an application of an embodiment of the corrosion rate detecting method of the present invention to detection of the rate of corrosion of a steel-pipe pile supporting a pier.

The present invention will be described with reference to measurement of the rate of corrosion of a steel-pipe pile supporting a pier in a harbour. As shown in FIG. 1, a detector 2 commonly used for detecting the rate of corrosion of metal materials is fixed to a corroded surface of a steel-pipe pile 3 by fixtures 4, and a measuring system 1 including a polarizing device is used together with a microcomputer 5 to measure the rate of corrosion of the surface of the pile 3 in a manner as described later.

Figure 2A:
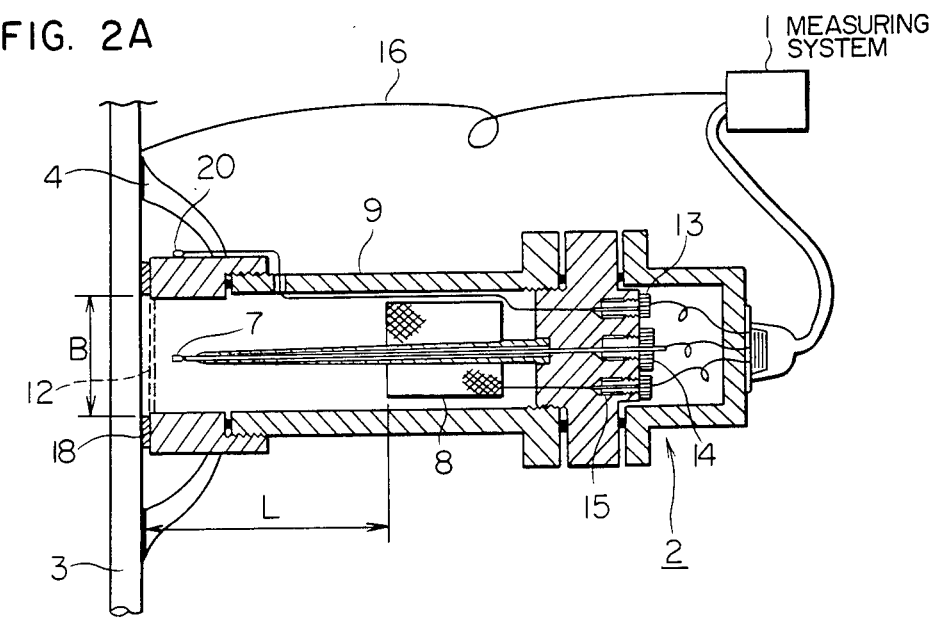
FIG. 2A shows schematically the structure of a corrosion rate detector preferably used in the method of the present invention.

As shown in FIG. 2A, the corrosion rate detector 2 includes a cylindrical enclosure 9 of electrical insulating material having a circular end opening 12 adapted to make intimate engagement with the corroded surface of the steel-pipe pile 3 which is the object of measurement, a reference electrode 7 extending in the enclosure 9 along the central axis of the enclosure 9 with its front end being located in close proximity to the end opening 12 of the enclosure 9, and a cylindrical electrode 8 of platinum having its front end inwardly spaced more from the front end of the reference electrode 7 and having a cross-sectional area substantially equal to that of the enclosure 9. The detector 2 is fixed to the corroded surface of the steel-pipe pile 3 by the fixtures 4 which may be magnets. A sealing member 18 of silicon rubber or like material is fixedly mounted to the peripheral edge of the end opening 12 of the enclosure 9 so that the enclosure 9 makes water-tight intimate engagement at its end opening 12 with the corroded surface of the steel-pipe pile 3. The inner diameter B of the circular end opening 12 of the enclosure 9 is about 30 mm, the distance between the end opening 12 and the front end of the reference electrode 7 is about 4 mm to 30 mm, and the distance L between the end opening 12 and the front end of the platinum electrode 8 is larger than the inner diameter B of the end opening 12 and is about 100 mm. An auxiliary electrode 20 is used for monitoring the potential outside the enclosure 9 which should be maintained substantially constant before and during the measurement of AC impedance by applying voltage potential variation through the reference electrode 7 to the surface of the pile inside the enclosure, as mentioned hereinafter.

Figure 2B:
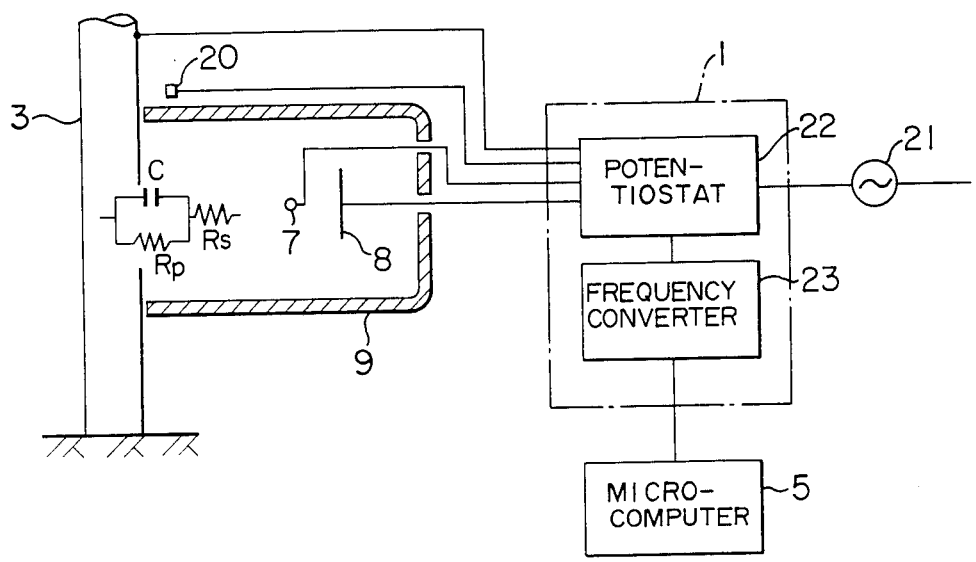
FIG. 2B shows schematically a measuring circuit preferably used for the practice of the method of the present invention.

FIG. 2B shows an outline of the measuring circuit using the corrosion rate detector 2 shown in FIG. 2A. The corroded surface of the steel-pipe pile 3 submerged in seawater forms an electrical double layer equivalently represented by a parallel circuit of an electrostatic capacitor C and a corrosion reaction resistance Rp (elution of Fe ions) and a resistance Rs connected in series to the parallel circuit depending on the rust layer and other materials deposited on the corroded surface of the pile 3.

21 designates an external AC power source and 22 designates a polarizing device of potential-control type including ampere meter and voltage meter and connected to the reference electrode 7, the platinum electrode 8 and the steel-pipe pile 3. 23 designates a frequency response analyzer which detects the surface natural potential of about $-550$ mV to $-600$ mV versus Ag/AgCl existing at the reference electrode in a natural submerged state of the pipe 3 and controls the polarizing device so as to produce, based on the surface natural potential, an AC potential variation so that the natural potential plus or minus an AC amplitude of 10 mV is applied through the reference electrode 7 to the surface of the pile 3 at its area specifically limitted by the corrosion rate detector 2 and measures an amount of the current response and a phase difference between the applied voltage and the current response.

The corrosion rate is determined according to the present invention by calculating AC impedances based on the applied voltage and the current response measured at specifically controlled frequencies of the applied voltage. This process of measurement may be automated by using a microcomputer 5 according to a program previously prepared and stored in the microcomputer 5. It will be seen from the equivalent circuit shown in FIG. 2B that, in the case of corrosion rate measurement by additional supply of the voltage of a high frequency, the value of the capacitance C can be regarded to be almost zero, and the value of the measured impedance is substantially represented by the value of the resistance Rs ($\Omega cm^2$). On the other hand, in the case of corrosion rate measurement by additional supply of the voltage of a low frequency, the value of the capacitance C can be regarded to be infinitely large, and the value of the measured impedance is substantially represented by the sum of the values of the resistances Rs and Rp. Therefore, the difference between these two measured values provides the value of the resistance Rp attributable to corrosion. In the above description, the value of the capacitance C is regarded to be substantially zero and substantially infinitely large in a high frequency range and a low frequency range respectively, and the values of the polarization impedance calculated on the basis of the measured voltage and current values represent the values of Rs and Rs+Rp respectively. Practically, the above calculation is sufficient for the purpose of calculation of the corrosion reaction resistance Rp. However, the corrosion reaction resistance Rp can be more accurately determined when, in order to remove the influence of the capacitance C, the phase difference between the voltage and the current is used to calculate the resistance component in the measured impedance for the calculation of Rs and Rs+Rp.

On the other hand, the relation between the corrosion-reaction current Icorr (A/cm$^2$) and the corrosion-reaction impedance Rp ($\Omega$cm$^2$) is experimentally determined as $Icorr = K/Rp$, where K is a constant whose unit is mV and which is about several mV to 20 mV although it differs depending on the environment and the metal material. Also, the relation between the corrosion-current (A/cm$^2$) and the rate of corrosion is experimentally determined as 40 $\mu$A/cm$^2$ = 0.47 mm/year. From the above relations, the rate of corrosion can be calculated.

The present invention is featured in that the impedance is measured in both a high frequency range and a low frequency range. For clarifying the feature of the present invention, the impedance was measured in a frequency range of 2 mHz to 1,000 Hz at three points per one decade. The results of the impedance measurement are plotted in FIG. 3, in which the abscissa represents the frequency in a logarithmic scale, and the ordinate represents the impedance in a logarithmic scale.

Figure 3:
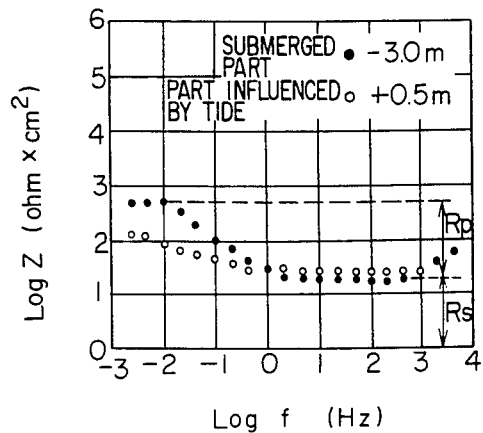
FIG. 3 is a graph showing the relation between the power supply frequency and the measured impedance value when the surface impedance of a corroded surface is measured by an AC impedance method.

The state of corrosion of the structural member of steel material partly submerged in seawater differs between a part kept submerged in seawater and a part subjected to the influence of tide, and such parts also show frequency response characteristics slightly different from each other. The curve depicted by black dots ● in FIG. 3 shows an example of the relation between the frequency and the impedance of the part kept submerged in seawater, and the curve depicted by white dots ○ shows that of the part subjected to the influence of tide. It will be seen that, in the case of the former curve, the curve is generally flat in a high frequency range of 10 Hz to 1,000 Hz and in a low frequency range of 2 mHz to 10 mHz, and this means that the impedance value is constant in such ranges. The former curve represents the value of the resistance Rs of a rust layer other deposits and surrounding seawater, and the latter curve represents the sum of the corrosion-reaction resistance Rp and the above-descrbed resistance Rs.

The difference between the impedance measured in the low frequency range and that measured in the high frequency range provides the corrosion-reaction resistance Rp. The impedance increases at frequencies higher than 1,000 Hz. This increase is due to the inductance of a cable as long as several-ten meters used to connect the detector 2 to the measuring system 1.

It will be seen in FIG. 3 that, in the case of the black-dot curve, the corrosion-reaction resistance Rp can be distinctly detected at a frequency of about 5 mHz. On the other hand, in the case of the white-dot curve, the impedance progressively increases toward the low frequency range of the frequency used for the measurement and does not become constant even if measured at a lower frequency of 2 mHz. However, in this case too, a good correlation between the frequency and the rate of corrosion can be obtained as shown in Table 1 without accompanying any problem as a matter of fact, even when the impedance value measured at about 5 mHz is substituted for the resistance Rp. Table 1 shows the coefficient of correlation between the rate of corrosion and the frequency used for the measurement when the value of Rp was determined from the value of Rp+Rs measured for each of a plurality of members of steel material using four different frequencies, and the rate of corrosion was calculated according to the aforementioned calculation formulas.

TABLE 1

| | Frequency used for detection of Rp (mHz) | | | |
| --- | --- | --- | --- | --- |
| | 2 | 5 | 10 | 20 |
| Coefficient of correlation | 0.72 | 0.81 | 0.77 | 0.65 |

In the measurement of the rate of corrosion of a steel-pipe pile as shown in FIG. 1, the frequency range used for the measurement is preferably divided into two frequency ranges, that is, a low frequency range of 2 mHz to 10 mHz and a high frequency range of 100 Hz to 1,000 Hz, and a corroded surface to be measured is preferably previously adjusted or treated so that an impedance value of 5 $\Omega$cm$^2$ to 50 $\Omega$cm$^2$ is obtained in the measurement with frequencies in the high frequency range.

Next, the reasons why these two limited frequency ranges are adopted and the corroded surface to be measured should be previously adjusted or treated so as to limit the impedance measured in the high frequency range to the value specified above, will be described in detail.

As described with reference to FIG. 3, the impedance measured in the low frequency range is the sum of the corrosion-reaction resistance Rp and the resistance Rs of seawater, rust and other deposits. Rust is formed on a steel material submerged in seawater, and, in the case of a structural member of steel material, submerged in seawater, its surface is rendered to be excessively rugged by corrosion. In such a case, the capacitive component increases due to, for example, ions adsorped to the surface of the structural member, and the frequency with which the resistance Rp is detected shifts toward a low frequency range.

Results of a test conducted on many structural members of steel material have proved that the frequency with which Rp is detected with desired accuracy is lower than and including 10 mHz and that, even if Rp may not be detected with the desired accuracy, the impedance measured at the frequency lower than and including 10 mHz shows a good correlation with the rate of corrosion as shown in Table 1.

However, when the rate of corrosion of a structural member of steel material is to be measured on site, the efficiency of measurement must be taken into consideration, and it is practically difficult to measure the rate of corrosion with a very low frequency. For example, a period of time as long as about 17 minutes is required for the measurement with frequencies between 2 mHz and 1,000 Hz, whereas a period of time of about 3 minutes and a half is required for the measurement with frequencies between 5 mHz and 1,000 Hz. A frequency range which provides a good correlation between the rate of corrosion and the impedance must be selected, and the period of time required for the measurement must also be as short as possible. From these aspects, an allowable lower limit of the frequency to be actually used in the in-field measurement of the rate of corrosion is 2 mHz.

Thus, when the measurement of the rate of corrosion of a structural member of steel material is considered, the optimum low frequency range used for the detection of the impedance which is the sum of the corrosion-reaction resistance Rp and the resistance Rs of seawater, rust and other deposits, is between 2 mHz and 10 mHz.

Further, the high frequency range used for the detection of the impedance, that is, the resistance Rs of seawater, rust and other deposits is theoretically higher than and including 1,000 Hz. However, in the case of measurement of a structural member of steel material, it is the present status that a cable as long as several-ten meters is inevitably used to connect the detector 2 to the measuring system 1 shown in FIG. 2A, due to the difficulty of reducing the scale and size of the measuring system.

Consequently, the inductance of the cable adversely affects the results of measurement with frequencies in a high frequency range, and errors due to the cable inductance are inevitably included in the results of measurement with frequencies higher than about 1,000 Hz. Depending on the condition of the cable used for the connection, an error may be included in the detected value of Rs when measurement is made with frequencies lower than 1,000 Hz. However, such an error is only about several percentages of the true value of Rs when the frequency used for the detection is closer to 100 Hz, and any practical problem would not arise.

In the graph shown in FIG. 3, the impedance curve is substantially flat in a high frequency range higher than about 10 Hz. However, the results of a test conducted on many other structural members of steel material have proved that the impedance curve of any one of the members is substantially flat in a frequency range higher than 100 Hz. Thus, the impedance in a high frequency range is preferably measured at frequencies between 100 Hz and 1,000 Hz.

As described already, a surface to be electrochemically measured is preferably adjusted or treated so that an impedance value of 5 $\Omega cm^2$ to 50 $\Omega cm^2$ is obtained when measured with a frequency between 100 Hz and 1,000 Hz. Such treatment is required so that an oxidation-reduction reaction occurring in, for example, a rust layer formed on the surface may not adversely affect the electrochemical measurement, and the measurement can be made under the same conditions at all times. Especially, the rust formed on an area of the steel surface subjected to the influence of tide has a composition different from that of the rust formed on the submerged area, and its bond to the steel surface is greater than that of the latter. Therefore, unless such rust is removed to leave a uniform rust layer on the steel surface, it leads to a measurement error.

The fact that the presence of rust and other deposits leads to a measurement error had not been considered before the test on many structural members of steel material was conducted. Deposits accumulating on the rust layer are preferably completely removed. However, it is unnecessary to completely remove the underlying rust layer. Complete removal of the rust layer to expose the steel surface analogous to a polished surface is rather undesirable in that the true rate of corrosion at the moment of on-site measurement cannot be detected.

According to a test conducted by the inventors, it is enough to treat the surface to be measured until an impedance value of 5 $\Omega cm^2$ to 50 $\Omega cm^2$ is obtained when measured with a frequency between 100 Hz and 1,000 Hz. For the purpose of this surface treatment, a tool such as a scaling bar or a scraper is preferably used to remove deposits. Polishing the steel surface with a tool such as a sander should be avoided for the reason described above.

EMBODIMENT

The object of corrosion rate measurement is a steel-pipe pile supporting a pier as shown in FIG. 1. This pile was periodically inspected for ten years, and the yearly rate of corrosion of the pile was already known. The rate of corrosion was measured for a plurality of depthwise divided parts of the pile, and the corrosion rate detector shown in FIG. 2A was used for the measurement.

The impedance in a low frequency range was measured with a frequency of 5 mHz, and the impedance in a high frequency range was measured with a frequency of 1,000 Hz.

Figure 4:
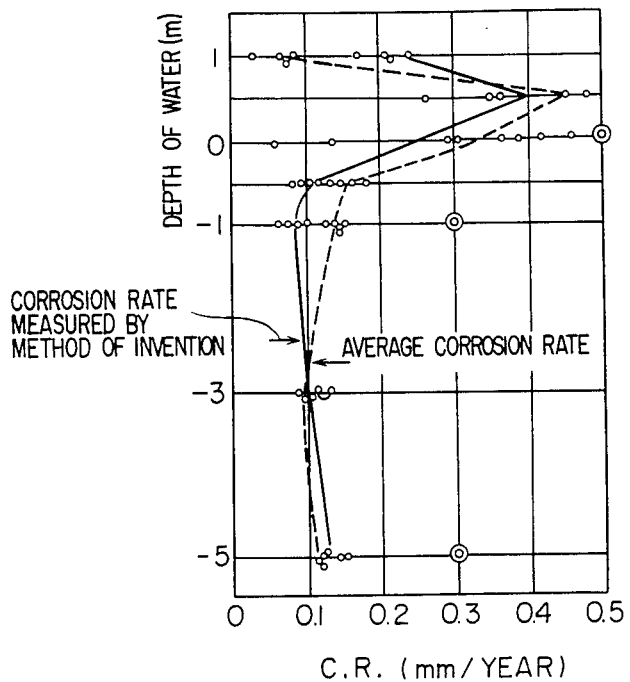
FIG. 4 is a graph showing a depthwise distribution of the rate of corrosion of a partly submerged structural member of steel material measured by the method of the present invention.

FIG. 4 is a graph showing the results of measurement of the rate of corrosion of the pile partly submerged in seawater. The ordinate represents the depth from LWL (low water level), and the abscissa represents the rate of corrosion. The solid curve in FIG. 4 represents the depthwise distribution of the rate of corrosion calculated on the basis of the resistance Rp given by the difference between the two impedance values described above. On the other hand, the broken curve in FIG. 4 represents the depthwise distribution of an average rate of corrosion calculated on the basis of the wall thickness of the pile.

It will be seen from comparison between these two curves that they are very similar to each other. This fact also agrees to the common knowledge that the corrosion rate in seawater environment is substantially unchanged with years, if the seawater environment is substantially unchanged. Thus, it can be seen that the rate of corrosion can be accurately detected by the corrosion rate evaluation method of the present invention.

The data plotted at the depths indicated by ◎ in FIG. 4 were measured under a condition where the value of Rs was larger than Rs=50 $\Omega cm^2$. It will be seen that the measured rate of corrosion shows different values unless Rs is adjusted to be 5 $\Omega cm^2$ to 50 $\Omega cm^2$ by surface treatment.

It will be understood from the foregoing detailed description that, in the present invention, the measuring frequency range is limited, that is, a frequency belonging to a low frequency range of 2 mHz to 10 mHz and a frequency belonging to a high frequency range of 100 Hz to 1,000 Hz are used for measurement, and the correlation between the impedance and the rate of corrosion is clarified. Therefore, the period of time required hitherto for measurement with frequencies in the intermediate frequency range is unnecessary so that the total period of time required for measurement can be greatly shortened. Further, the measurement is carried out under the same conditions at all times so that the accuracy of measurement of the rate of corrosion of structural members of steel material can be improved.

According to the present invention, a device such as a corrosion rate detector which can directly detect the rate of corrosion of metal materials on the site is used for detecting the rate of corrosion of a structural member of steel material partly submerged in seawater, so that the period of time required for the measurement can be shortened. Further, the measurement is carried out under the same conditions at all times so as to improve the accuracy of measurement. Since the efficiency of measurement can be improved, an increased number of parts of the structural member can be measured so that deterioration attributable to corrosion can be more accurately diagnosed.

We claim:

1. A method of detecting the rate of corrosion of an existing steel structure installed in a corrosive environment, said steel structure having a surface section to which a probe is to be attached for detecting said corrosion rate, said method comprising the steps of:

removing deposits from said surface section of said steel structure so that an AC impedance of said surface section, when electrochemically measured by application of potential variation thereto at a predetermined high frequency range, takes a first value within a range of 5 $\Omega cm^2$ to 50 $\Omega cm^2$;

measuring the impedance of said measurement surface by application of potential variation at a predetermined low frequency range to obtain a second AC impedance value;

calculating the difference between said first and second measured values to detect a corrosion-reaction resistance of said surface section; and determining the rate of corrosion of said surface section on the basis of said detected corrosion-reaction resistance of said surface section and according to a precalculation relation between the rate of corrosion and the corrosion-reaction resistance;

whereby the corrosion rate can be determined directly on said surface section without the need for a separate corrodible testing means.

2. A method according to claim 1, wherein said high frequency range is 100 Hz to 1,000 Hz.

3. A method according to claim 2, wherein said low frequency range is 2 mHz to 10 mHz.

* * * * *